United States Patent
Cellura

(10) Patent No.: US 8,595,026 B2
(45) Date of Patent: Nov. 26, 2013

(54) SYSTEM AND METHODS OF OBTAINING REIMBURSEMENTS FOR PATIENT TREATMENT

(75) Inventor: Alfred Cellura, Rochester, NY (US)

(73) Assignee: Global Health Products, Inc., Rochester, NY (US)

( * ) Notice: Subject to any disclaimer, the term of this patent is extended or adjusted under 35 U.S.C. 154(b) by 954 days.

(21) Appl. No.: 12/034,902

(22) Filed: Feb. 21, 2008

(65) Prior Publication Data
US 2009/0216553 A1 Aug. 27, 2009

(51) Int. Cl.
*G06Q 50/00* (2012.01)

(52) U.S. Cl.
USPC .......................................................... 705/2

(58) Field of Classification Search
USPC ........................................................ 705/2–4
See application file for complete search history.

(56) References Cited

U.S. PATENT DOCUMENTS

| | | | |
|---|---|---|---|
| 5,480,865 A | 1/1996 | Kingham | |
| 5,612,074 A | 3/1997 | Leach | |
| 6,004,926 A | 12/1999 | Shimizu et al. | |
| 6,014,632 A | 1/2000 | Gamble et al. | |
| 6,297,420 B1 * | 10/2001 | Heincke | 602/41 |
| 6,353,817 B1 | 3/2002 | Jacobs et al. | |
| 6,826,536 B1 | 11/2004 | Forman | |
| 7,038,588 B2 | 5/2006 | Boone et al. | |
| 7,069,227 B1 | 6/2006 | Lintel, III et al. | |
| 2004/0082502 A1 | 4/2004 | Gans | |
| 2008/0243547 A1 * | 10/2008 | Brett et al. | 705/3 |

OTHER PUBLICATIONS http://www.woundcareshop.com (published on Jul. 26, 2007) (from the Wayback Macine) (see printout).*

\* cited by examiner

*Primary Examiner* — John Pauls
(74) *Attorney, Agent, or Firm* — Brian B. Shaw, Esq.; Harter Secrest & Emery LLP

(57) ABSTRACT

A method of selecting a dressing for treating a patient's wound includes providing a database of dressings and dressing information corresponding to each dressing, the dressing information including an indication of whether the dressing is reimbursable. The method also includes observing a patient's wound, recording characteristics of the patient's wound, comparing the characteristics of the patient's wound to the database, displaying to a user a list of one or more dressings usable for treating the wound, and an indication of whether the dressing is reimbursable. The method further includes selecting a dressing for treating the wound from the list.

27 Claims, 3 Drawing Sheets

SYSTEM AND METHODS OF OBTAINING REIMBURSEMENTS FOR PATIENT TREATMENT

TECHNICAL FIELD

The present invention relates generally to patient care. More specifically, the invention relates to an automated system for treating patient wounds with dressings, the purchase price of which dressings may be reimbursable through an insurance program.

BACKGROUND OF THE INVENTION

Health insurance plans are well known. Medicare, for example, is a publicly-funded health insurance plan that generally covers medical expenses for people over some pre-determined age or having some pre-determined condition. Privately-funded health insurance plans also are known. Conventional plans, whether publicly- or privately-funded generally will provide coverage for outpatient or nursing home care, including payment for services rendered and reimbursement for products used in conjunction with services.

To receive their reimbursements, caregivers generally submit a claim and often supporting documentation to the insurance provider. The insurance provider then determines whether the service and/or products are covered by the policy, and pays and/or reimburses the caregiver, as appropriate. Medicare, for example, maintains and provides lists of services and products that will be reimbursed for treatment of specific maladies.

However, the inventors have found that many institutions, and particularly many nursing homes, are ill-equipped to receive maximum reimbursements, especially for day-to-day medical devices, such as bandages, dressings, and other disposable goods. Because no system exists for maximizing these reimbursements, such nursing homes generally consider the costs of these items to be normal operating expenses, or more likely, pass along the costs of these items to the patient.

Accordingly, there is a need in the art for a system for and method of maximizing reimbursements for patient care. There also is a need in the art for a method of selecting a reimbursable medical device for treating a patient.

SUMMARY OF THE INVENTION

The present invention remedies the foregoing needs in the art by providing a system for and methods of selecting reimbursable medical devices.

In one aspect of the invention, a method is provided for selecting a dressing for treating a patient's wound. The method includes providing a database of dressings and dressing information corresponding to each dressing, the dressing information including an indication of whether the dressing is reimbursable. The method also includes observing a patient's wound, recording characteristics of the patient's wound, comparing the characteristics of the patient's wound to the database, displaying to a user a list of one or more dressings usable fro treating the wound and an indication of whether the dressing is reimbursable. The method further includes selecting a dressing from the list for treating the wound.

In another aspect of the invention, a method is provided for treating a wound that includes classifying a wound, selecting a dressing to treat the wound, determining whether treatment of the wound classification is reimbursable by an insurer, determining whether the selected dressing is reimbursable by the insurer for treatment of the wound, and ordering the dressing.

These and other aspects and features of the invention may be had with reference to the accompanying description and figures, in which preferred embodiments of the invention are described and illustrated.

BRIEF DESCRIPTION OF THE DRAWING FIGURES

DETAILED DESCRIPTION OF THE INVENTION

The present invention generally provides a method for treating patients, which treatment may include diagnosis, medication administration, surgery, post-surgery care, and the like. More specifically, the invention relates to systems and methods for maximizing reimbursements for such treatments and instrumentalities used in connection with those treatments. The preferred embodiments of the invention describe a procedure for selecting and ultimately obtaining reimbursement for a dressing for a wound. However, the invention is not limited to reimbursable dressings. As will be appreciated by those of skill in the art, the systems and methods described in this application may be useful for selecting and obtaining reimbursement for any number of treatments and instrumentalities.

Figure 1:
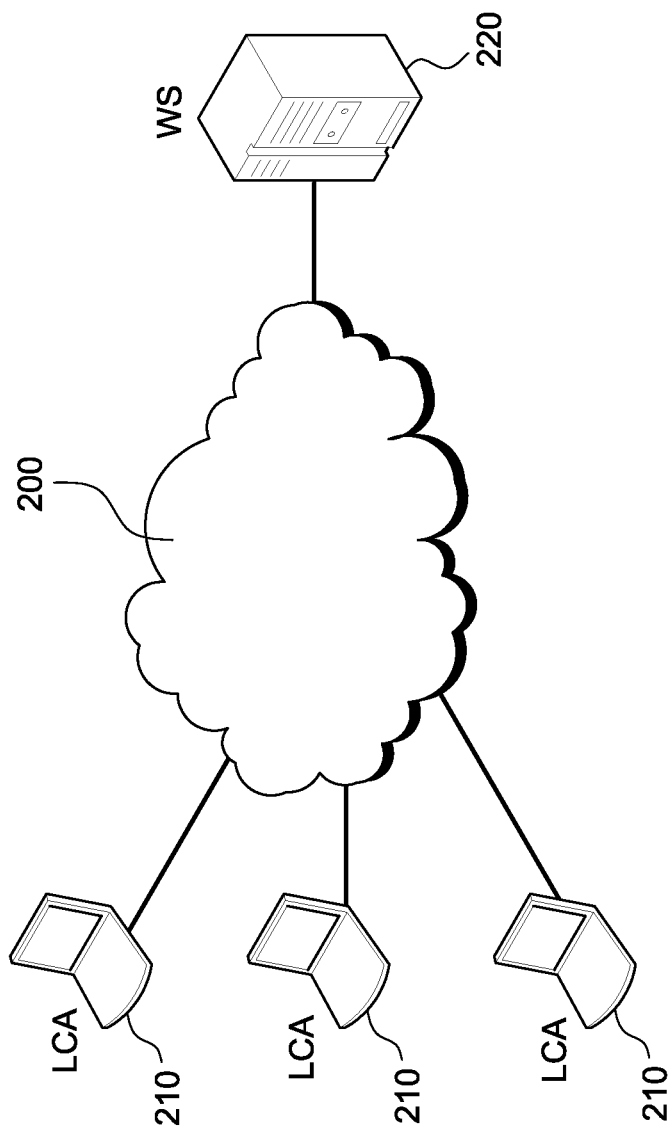
FIG. 1 is a schematic diagram illustrating a preferred computer system used for implementing preferred embodiments of the present invention.

The systems according to the invention preferably are implemented using a computer system. The computer system includes a number of computers capable of transferring information therebetween, e.g., via a network, or the like. As illustrated in FIG. 1, the computer system may include a client server 200, one or more client, local computers 210 and a remote server 220 communicating via the internet 200. As will be appreciated by one of ordinary skill in the art from the following discussion, the invention is well suited for use with the computer system of FIG. 1, but is not limited to this system. Other methodologies will be readily understood by one of ordinary skill in the art for implementing the invention. For example, other means for transferring data between computer systems are well known, including but not limited to, public networks, private networks and wireless communication. Another implementation of the invention may also include one or more intermediate servers on which additional data may be stored. Moreover, the remote server 220 may alternatively by stored in the same facility, e.g., nursing home, in which the local computers 210 are used, in which case the internet may be less desirable than a local wireless, e.g., blue-tooth, or direct-wired connection.

One or both of the local computer 210 and the remote server 220 preferably stores databases containing information about wounds, dressings, and insurance plan particulars. This and other information may be stored in a single database, or in multiple, different databases. For example, a dressing database preferably includes a number of dressings, along with information about which wound types the dressings are used to treat. This database also may include additional information about the dressings, including reimbursement information indicating whether the dressing is reimbursable. Other information included in the database may include but is not limited to, the manufacturer of the dressing, the distributor of the dressing, the price, the stock number, ordering information, an image of the dressing, or any other useful information. A wound database described above preferably includes cross-references of wound characteristics to wound types, such that when the user inputs wound characteristics, the database can be used to determine the type of wound. Other information also may be stored on the client server, either in already existing databases, or in additional databases. For example, the client server may store files or charts for all patients being treated. Also, insurance information may be stored in a patient-by-patient database, to the extent necessary.

The local computers preferably are personal computers, e.g., laptops or desktop computers, that may be carried or otherwise transported from patient to patient. Each local computer preferably can readily display a client chart by retrieving the chart from the local database. Client charts may be stored on one or both of the local computers 210 and the remote computers 220. A caregiver uses one of the local computers to enter data about each patient, thereby updating the patient's chart.

The remote server preferably provides updates to the software and other information stored on the client computers. For example, when new dressings are to be added, or information relating to existing dressings changes, an update can be effected at the remote server, and transmitted to each of a plurality of registered client servers or local computers.

As illustrated in FIG. 1, the local computers preferably are connected to the internet or some other network to communicate with the remote server. This internet connection may also preferably be connected to the internet to access third parties. For example, and as will be described in more detail below, it may be desirable to order dressings automatically from a vendor or distributor in the network connection. In addition, the local computer may communicate with the insurance company to automatically forward reimbursement requests, supporting documents, or the like, although this could alternatively be done from the host server. An additional, intermediate server may also be present at the client, for example, to collect data from all of the local computers and place only a single order or submit all reimbursement requests.

Figure 2:
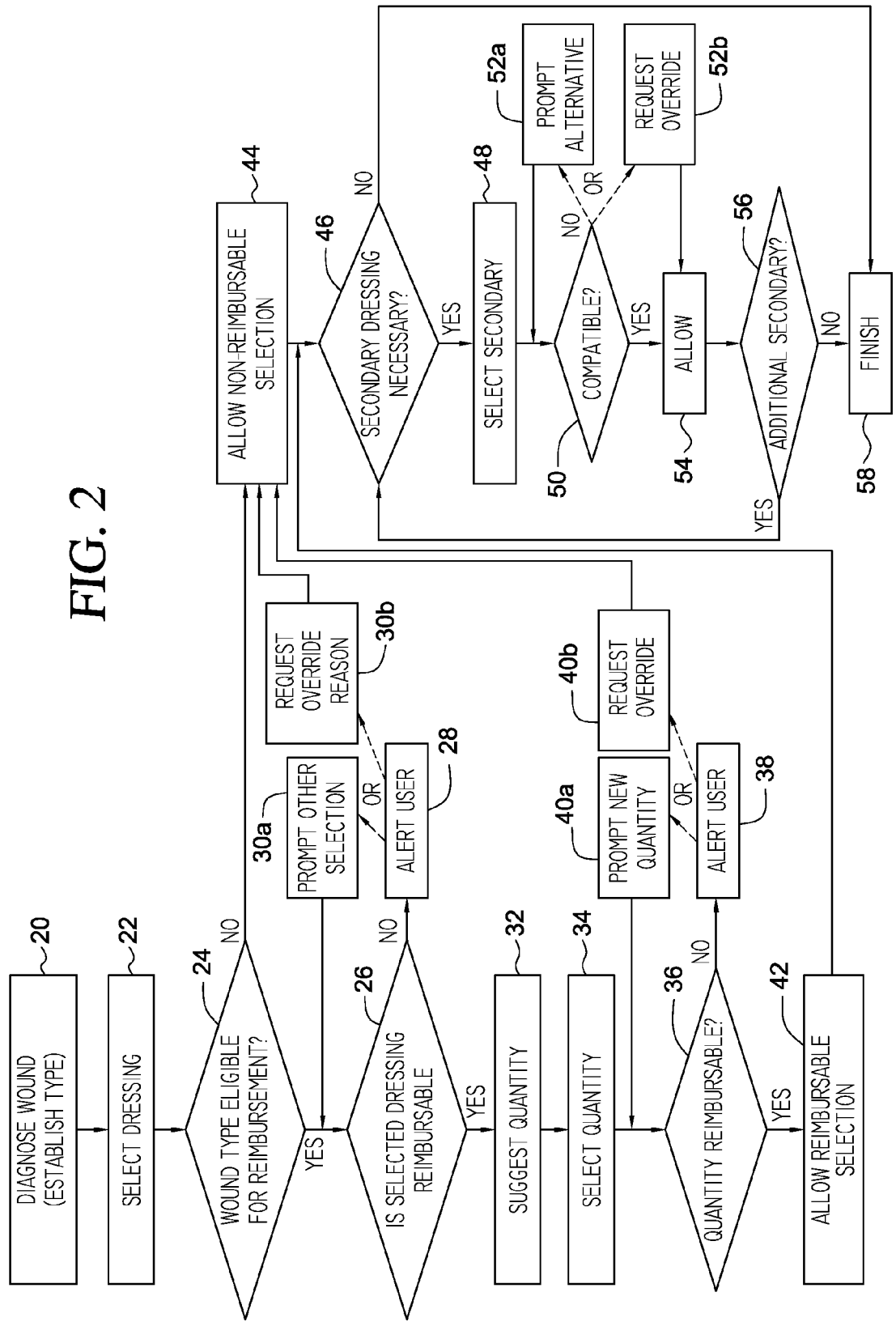
FIG. 2 is a flowchart showing a method of assisting foreigners with selection of dressings for wounds to maximize reimbursement of the purchase price of such purchase price.

FIG. 2 is a flow chart describing a preferred method of selecting and obtaining reimbursement for a dressing for a wound using the system described with reference to FIG. 1. In step 20, a patient's wound is observed by a caregiver, namely a doctor, nurse, technician, or the like. The caregiver generally looks to the size, shape, coloration, discharge, and/or other characteristics of the wound, and based on these observations, determines a type or stage of the wound in step 20. For example, it is generally known to classify wounds by numbered stages, namely, stages 1-4, or as surgical site wounds, although other classification schemas may also be used. These classifications also are used by many insurance plans, and, as will be described in more detail below, according to those plans only certain dressings may be reimbursable for each stage or type of wound and some stages may not be covered at all.

The type of wound generally is determined by the expertise of the caregiver. However, step 20 may be done automatically using the computer system. Specifically, in one embodiment, the computer may contain a database of wound types and their associated characteristics, such that the caregiver may enter into one of the local computers the observed wound characteristics, and the computer will automatically generate the type of wound.

The wound classification is entered into the local computer and once classified, a course of treatment is determined by the caregiver. This course of treatment includes selecting a dressing for the wound in step 22. In addition to entering the wound classification determined in step 20, the caregiver also may enter other information, or particulars about the wound, for example, to track healing of the wound.

In step 24, a database is searched to determine whether treatment of the wound classification is eligible for reimbursement. For example, treatment of some wound stages may be not be reimbursable, perhaps because the wound is too minor to warrant insurance coverage. If treatment of the wound type is not reimbursable, the caregiver is informed that the dressing selected will not be reimbursed by the insurance provider, and, preferably, that no dressing will be reimbursed for this wound type. The caregiver is then allowed in step 44 to continue on with ordering the selected dressing, including, by selecting a quantity of the non-reimbursed dressing to be ordered.

If it is determined in step 24 that treatment of the wound is reimbursable, a determination is made in step 26 as to whether the dressing selected by the caregiver is a reimbursable dressing for the wound-type. Preferably, the selected dressing is checked against dressing information contained in a database. If the selected dressing is not a reimbursable dressing, the caregiver is alerted to the fact that the dressing is not reimbursable, in step 28, and is prompted either to select a new dressing (step 30a) or to provide a reason for ordering a non-reimbursable dressing (step 30b). If a new dressing is selected, processing is returned to step 26 to determine whether the newly chosen dressing is reimbursable. If the caregiver insists on ordering the non-reimbursable dressing, the reason for doing so is saved, and ordering of the non-reimbursed dressing is allowed, in step 44.

If the dressing selected is reimbursable, the caregiver is then preferably presented with a suggested quantity of that dressing for ordering, in step 32. The suggested quantity preferably is derived from stored information, including information about how frequently the dressing should be changed and the maximum number of dressings reimbursed under the insurance plan. Under most circumstances, the suggested quantity preferably is the maximum number of dressings that are reimbursable according to the insurance plan. Additional information also may be presented to the user, including, but not limited to, information about use of the dressing and/or other detailed information about the selected dressing.

In step 34, the user then enters the quantity desired, either by accepting the suggested quantity or by entering another quantity for ordering. In step 36, a determination is made as to whether the quantity is a reimbursable quantity. In step 38, the system alerts the caregiver if the quantity entered exceeds the number of dressings that will be reimbursed by the insurance plan. When so alerted, the caregiver preferably is given the opportunity to either revise the requested quantity (step 40a), or input a reason for requesting the non-reimbursed quantity (step 40b). If the desired quantity is revised, processing is returned to step 36 to verify acceptance of the new quantity. If the caregiver opts to proceed with a non-refundable quantity, the reason for requesting this quantity is logged and processing advances to step 44, where the selection of a non-reimbursable quantity is allowed. If the quantity selected is reimbursable, processing proceeds to step 42, where selection of a reimbursable quantity of a reimbursable dressing is approved.

Processing from either of steps 42 or 44 advances to step 46 in which the caregiver is offered the ability to select a secondary dressing. If no secondary dressing is required, processing is concluded at step 58. If, however, a secondary dressing is desired, the caregiver selects a secondary dressing in step 48, and the system processes the selection to determine whether the selected secondary dressing is compatible with the primary dressing in step 50. Specifically, the system preferably stores information about compatibility between primary and secondary dressings and alerts the user when the selected secondary dressing is incompatible. In another preferred embodiment, the system will provide to the caregiver a suggested secondary dressing, based on information stored in the database about the compatibility of dressings. If the secondary dressing is compatible with the primary dressing, the selection is allowed in step 54 and processing advances to step 56. If the secondary dressing is not compatible with the primary dressing, the user is asked to enter a reason for ordering a non-compatible dressing in step 52b, the order is allowed in step 54, and processing advances to step 56. Alternatively, the user may be presented with a new list of secondary dressings (or the same list again) (in step 52a) for selection of an alternative dressing. In step 56, the user is asked to enter another secondary dressing. If additional secondary dressings are to be entered, processing returns to step 48, where another dressing is selected. If no additional dressings are to be ordered, processing is completed in step 58.

Figure 3:
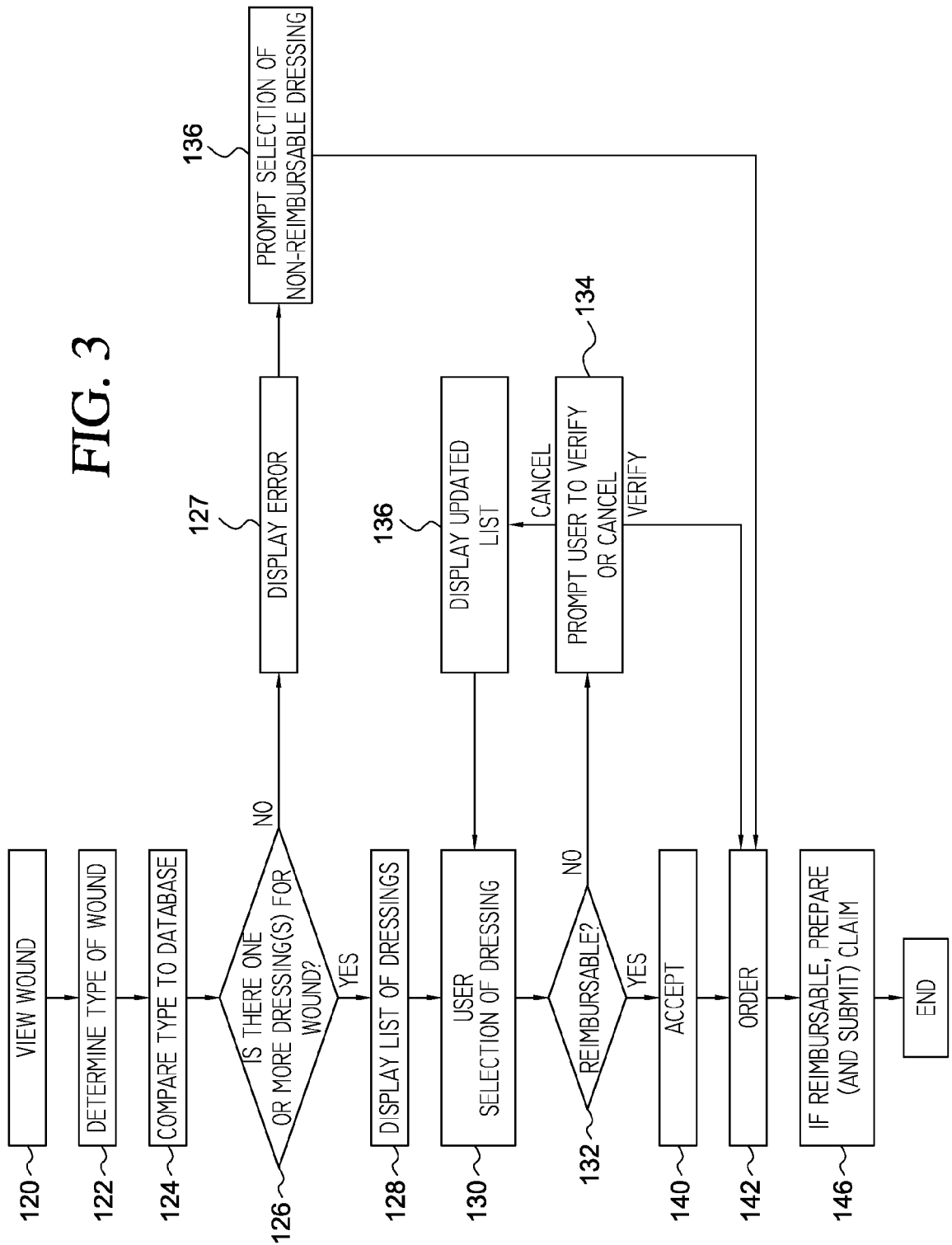
FIG. 3 is a flowchart showing another embodiment of the invention.

An alternative processing embodiment now will be described with reference to FIG. 3. In FIG. 3, in step 120 the wound is diagnosed by the caregiver and a wound type is determined in step 122, as in the previous embodiment. In step 124, the wound type is entered into the user interface by the caregiver and the wound type is compared to the database containing dressings used for treating various wound types. As a result of the comparison, one or more dressings for treating the wound are automatically determined in step 126. Thus, in this embodiment, the caregiver is provided with a specific list of dressings for input wound information. The dressings determined may be generic descriptions of the dressing, or, more preferably, the dressings may be actual products. To this end, in addition to storing data relating wound types to dressings, and as described above, the database also preferably includes information about the dressing. This information preferably includes reimbursement information indicating whether the dressing will be reimbursed by an insurance plan. The information also may include, but is not limited to, tradename, stock number, manufacturer, distributor, contact information for the distributor.

If in step 126 no dressing for treating the wound can be determined, e.g., because treatment of the wound is not reimbursable, an error message preferably is displayed to the user in step 127. The user may then be prompted to confirm the entered wound type, to ensure the wound type was not entered in error. The user preferably then, in step 136, is presented with a list of dressing for selection without reimbursement.

In step 128, a list of the dressings determined in step 126 is provided to the user, and in step 130, the user selects the desired dressing from the list. Preferably, the list is displayed on the same user interface used to record observations regarding the patient. In addition to listing the dressing(s) usable for treating the wound, the list also may include any of the information about the dressing(s) stored in the dressing database.

Upon selection of a dressing from the list, a determination then is made in step 132 as to whether the selected dressing is a reimbursable dressing, namely, whether the insurance provider covers usage of the selected dressing for treating the wound. Preferably, this determination is made by simply checking the reimbursement information associated with each dressing and stored in the database. If the dressing selected in step 130 is determined in step 132 to be reimbursable, the selection is accepted in step 140.

If, in step 132, a determination is made that the selected dressing is not reimbursable, the user is prompted in step 134 to verify their choice of dressing, because the selected dressing is not reimbursable. Preferably, the user is alerted to the fact that the selected dressing is not reimbursable by a pop-up window, a new screen, a graphic, or the like, which requires the user either to confirm or cancel their selection of the non-reimbursable dressing.

If the user confirms their selection, the non-reimbursable dressing is accepted in step 140. However, if the user cancels their choice of selected dressing when prompted in step 134, a new list is provided to the user in step 136. The new list may be the original list, or the original list with the previously-selected dressing being removed or otherwise incapable of being again selected. In another embodiment, the new list presented in step 136 may be a list of only those dressings that are reimbursable. In yet another embodiment, the original list may be a single dressing available from a selected supplier, e.g., the host of the system or a preferred vendor, with a user having to decline that dressing to select another either reimbursable or non-reimbursable dressing.

Once presented with the new list in step 136, processing returns to step 130, where the user makes a selection from the new list. The process thereafter returns to step 132 where it is determined whether the newly selected dressing is reimbursable. If the selected dressing is not reimbursable, processing proceeds again to step 134 to prompt the user that their selection will not be reimbursed by the insurance provider.

As noted above, if the determination made in step 132 is that the selected dressing is reimbursable, the selection is accepted in step 140. Upon acceptance, the selected dressing is ordered in step 142, and a reimbursement request is generated and processed in step 146.

With the described computer system, the process described above with reference to FIG. 1 preferably is carried out as follows. When doing periodic rounds to check in on patients, a caregiver takes with him one of the local computers 210. At the bedside of each patient, the caregiver calls up the patient's chart, which may be maintained on the remote server and/or on the local computer. The caregiver views the patient's wound(s) and enters specifics about the wound into the system. These specifics may be a detailed description of the wound, in which case the computer preferably checks a wound database that may be stored on the remote server, the local computer, and/or some intermediate server, to determine a stage or type of the wound, or the specifics may simply be a stage or type of the wound, as determined by the caregiver.

With the type of wound established, the local computer then communicates with the remote server, which checks the wound type against the stored dressing database. Based on this comparison, it is determined whether one or more dressings are available to treat the wound, and a list of the dressings is displayed to the caregiver on the local computer. A determination also may be made as to whether to treatment of the wound type is reimbursable.

The user then selects one of the dressings using some conventional selecting device, such as a mouse, keyboard, or touch screen, for example. The local computer preferably then corresponds with the local database to check reimbursement information stored in the database corresponding to the selected dressing, to determine whether the dressing is reimbursable, i.e., based on the wound type and dressing selection.

If the dressing is reimbursable, the selection is accepted, the client server corresponds with a vendor or distributor to order the selected dressing and the client server generates necessary documentation and forwards that documentation to the product distributor to request reimbursement. If the selected dressing is not reimbursable, an alert pops-up on the monitor of the local computer 210, informs the user that the selected dressing is not reimbursable, and prompts the user to either confirm or cancel their selection. Using the conventional selecting device described above, the user confirms the selection, in which case, the selection is accepted, and the dressing is ordered by the client server, or the user cancels the selection. Upon cancellation, the local computer displays a new list and the user selects a different dressing from the new list. When the different dressing is confirmed to be reimbursable, the selection is accepted, the remote server corresponds with a vendor or distributor to order the selected dressing and the remote server generates necessary documentation. This documentation may be collected by the product distributor, or it may be forwarded via a network to the insurance provider to request reimbursement.

Many variations to the above-described processes also are contemplated. For example, a determination may be made prior to showing a list of dressings as to whether any of the dressings for the wound are reimbursable, i.e., by checking reimbursement information associated with each dressing. Then, when a list of the available dressings is displayed, the list preferably only includes those dressings that are reimbursable. Alternatively, the list may include all dressings, but in some way designate those dressings that are reimbursable. For example, the dressings that are reimbursable may be listed altogether and separate from the non-reimbursable dressings, or the dressings may be highlighted in some manner. Alternatively, a word, mark, or other indicia may be used in conjunction with the listed dressing to indicate that a dressing is reimbursable.

The foregoing embodiments of the invention are representative embodiments, and are provided for illustrative purposes. The embodiments are not intended to limit the scope of the invention. Variations and modifications are apparent from a reading of the preceding description and are included within the scope of the invention. The invention is intended to be limited only by the scope of the accompanying claims.

The invention claimed is:

1. Method of selecting a dressing for treating a patient's wound, comprising:
providing a database of dressings and dressing information corresponding to each dressing, the dressing information including an indication of which wound types a dressing will dress whether the dressing is reimbursable and for which applications the dressing is reimbursable;
comparing a patient's wound type to the database;
displaying on a digital display to a user a list, based on the comparing step, of one or more recommended dressings usable for treating the wound together with an indication of whether the recommended dressing is reimbursable for the patient's wound;
receiving a user input corresponding to a selection of a dressing from the list; and
displaying to the user, on the digital display when the user has selected a dressing that is reimbursable, a second list of secondary dressings, each of the secondary dressings being complementary to the selected dressing; and
receiving a user input corresponding to a selection of a secondary dressing from the second list.

2. The method of claim 1, further comprising ordering automatically one of the selected dressing and the selected secondary dressings from a third party.

3. The method of claim 1, wherein each of the one or more dressings on the list is a reimbursable dressing.

4. The method of claim 1, wherein the one or more dressings on the list are displayed in an order of recommended usage.

5. The method of claim 1, wherein the list consists of a single recommended dressing.

6. The method of claim 5, further comprising displaying a secondary list of dressings comprising one or more dressings for treating the wound upon a rejection of the recommended dressing.

7. The method of claim 5, further comprising prompting the user to provide reasons for rejecting the recommended dressing upon a rejection of the recommended dressing.

8. The method of claim 7, wherein prompting the user comprises displaying a questionnaire for completion by the user.

9. The method of claim 1, wherein the displaying step further comprises displaying a quantity of the dressing, the quantity being the number of dressings that is reimbursable.

10. The method of claim 9, further comprising prompting a user to enter a reason when the user selects a non-reimbursable quantity of the dressings.

11. The method of claim 1, further comprising upon selection by a user of a displayed dressing comprising a primary dressing;
displaying on the digital display to the user at least one secondary dressing compatible with the selected primary dressing and an indication of whether the secondary dressing is reimbursable.

12. A method of treating a patient comprising:
monitoring a wound of the patient at intervals;
recording characteristics of the wound at each of the intervals;
comparing the recorded characteristics of the wound to a database containing predetermined wound treatment information corresponding to wound characteristics; and
receiving, via a display on a digital display, the predetermined treatment information corresponding to the recorded characteristics as a treatment methodology including a first treatment methodology including at least a first dressing and a second, complementary treatment methodology including at least a second dressing.

13. The method of claim 12, wherein the characteristics of the wound include one or more of shape, color, discharge, and size.

14. The method of claim 12, wherein the receiving step comprises receiving a list of treatment options.

15. The method of claim 14, further comprising a step of selecting one of the treatment options from the list of treatment options.

16. The method of claim 15, each of the dressings having reimbursement information associated therewith.

17. The method of claim 16, wherein the dressing and the associated reimbursement information are displayed on the list of treatment options.

18. The method of claim 17, further comprising selecting a dressing from the list.

19. The method of claim 18, further comprising purchasing the selected dressing.

20. The method of claim 12, wherein the predetermined treatment information comprises one or more treatments and the treatments are displayed to the user in the recording step, and further comprising the step of selecting one of the treatments.

21. A method of selecting a medical device comprising:
monitoring a malady of a patient;
recording characteristics of the monitored malady;
comparing the recorded characteristics to a database containing treatments for maladies, each of the treatments comprising a dressing, each dressing having associated reimbursement information indicating whether the dressing is reimbursable;
selecting a dressing from a displayed list of the dressings capable of treating the malady and the associated reimbursement information, the displayed list being provided on a digital display;
ordering the selected dressing from a supplier;
providing a reason for selecting the selected dressing when the reimbursement information associated with the selected dressing indicates that the selected dressing is not reimbursable; and
requesting a reimbursement for the selected dressing when the reimbursement information associated with the selected dressing indicates that the selected dressing is reimbursable.

22. The method of claim 21, further comprising receiving an alert when the reimbursement information associated with the selected dressing indicates that the selected dressing is not reimbursable.

23. The method of claim 21, wherein only the dressings that are reimbursable are contained on the displayed list.

24. The method of claim 21, wherein one dressing is contained on the displayed list.

25. The method of claim 24, further comprising accepting or rejecting the one dressing.

26. The method of claim 25, wherein when the one dressing is rejected, a secondary list is displayed having additional dressings capable of treating the malady.

27. A method of selecting a dressing for a wound comprising:
providing a database of dressings and dressing information corresponding to each dressing, the dressing information including an indication of whether the dressing is reimbursable, and the database including correspondence between a dressing and a type of wound;
observing a patient's wound;
determining a type of the wound;
comparing the type of the wound to the database;
displaying on a digital display to a user a list, based on the comparing step, of one or more dressings usable for treating the wound;
selecting a dressing from the list of one or more dressings;
indicating whether the dressing is reimbursable; and
prompting a user to enter a reason for the user's selection when the user selects a non-reimbursable dressing.

* * * * *